United States Patent
Kim et al.

(10) Patent No.: US 10,435,347 B2
(45) Date of Patent: Oct. 8, 2019

(54) METHOD FOR PREPARING ACRYLIC ACID FROM GLYCERIN

(71) Applicant: LG CHEM, LTD., Seoul (KR)

(72) Inventors: Kyung Soo Kim, Daejeon (KR); Jun Seon Choi, Daejeon (KR); Ji Yeon Kim, Daejeon (KR); Joo Young Cheon, Daejeon (KR); Wang Rae Joe, Daejeon (KR); Hye Jeong Ok, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/762,868

(22) PCT Filed: Dec. 15, 2016

(86) PCT No.: PCT/KR2016/014740
§ 371 (c)(1),
(2) Date: Mar. 23, 2018

(87) PCT Pub. No.: WO2017/111391
PCT Pub. Date: Jun. 29, 2017

(65) Prior Publication Data
US 2018/0273460 A1    Sep. 27, 2018

(30) Foreign Application Priority Data

Dec. 23, 2015 (KR) .................. 10-2015-0184612
Oct. 25, 2016 (KR) .................. 10-2016-0139259

(51) Int. Cl.
*C07C 51/25* (2006.01)
*C07C 45/52* (2006.01)
*B01J 23/888* (2006.01)
*B01J 27/198* (2006.01)

(52) U.S. Cl.
CPC ......... *C07C 51/252* (2013.01); *B01J 23/8885* (2013.01); *B01J 27/198* (2013.01); *C07C 45/52* (2013.01)

(58) Field of Classification Search
CPC .... C07C 51/252; C07C 45/52; B01J 23/8885; B01J 27/198
See application file for complete search history.

(56) References Cited

U.S. PATENT DOCUMENTS

| | | | |
|---|---|---|---|
| 4,792,620 A * | 12/1988 | Paulik | B01J 31/0231 |
| | | | 560/232 |
| 7,396,962 B1 | 7/2008 | Dubois et al. | |
| 7,655,818 B2 | 2/2010 | Dubois et al. | |
| 7,880,034 B2 | 2/2011 | Dubois | |
| 8,076,509 B2 | 12/2011 | Kasuga et al. | |
| 8,252,960 B2 | 8/2012 | Dubois et al. | |
| 8,609,904 B2 | 12/2013 | Devaux et al. | |
| 8,829,246 B2 | 9/2014 | Dubois | |
| 8,962,881 B2 | 2/2015 | Tanimoto et al. | |
| 9,296,676 B2 | 3/2016 | Devaux et al. | |
| 9,321,040 B2 | 4/2016 | Joe et al. | |
| 9,327,276 B2 | 5/2016 | Choi et al. | |
| 9,546,124 B2 | 1/2017 | Lee et al. | |
| 2005/0070736 A1 | 3/2005 | Kang et al. | |
| 2008/0146852 A1 | 6/2008 | Dubois et al. | |
| 2008/0183013 A1 | 7/2008 | Dubois et al. | |
| 2009/0118549 A1 | 5/2009 | Matsunami et al. | |
| 2010/0010260 A1 | 1/2010 | Kasuga et al. | |
| 2011/0288323 A1 | 11/2011 | Belliere-Baca et al. | |
| 2013/0053595 A1 | 2/2013 | Magatani et al. | |
| 2013/0066100 A1 | 3/2013 | Magatani et al. | |
| 2017/0304804 A1 | 10/2017 | Kim et al. | |

FOREIGN PATENT DOCUMENTS

| | | | | |
|---|---|---|---|---|
| EP | 3189892 A1 * | 7/2017 | ............ | B01J 37/033 |
| EP | 3189892 A1 | 7/2017 | | |
| JP | 2008-162907 A | 7/2008 | | |
| JP | 2008-538781 A | 11/2008 | | |
| JP | WO2008-066079 A1 | 3/2010 | | |
| JP | 2011-518111 A | 6/2011 | | |
| JP | 2013040179 A | 2/2013 | | |
| JP | 2013-508127 A | 3/2013 | | |
| JP | 5305827 B2 | 10/2013 | | |
| JP | 5450591 B2 | 3/2014 | | |
| JP | 2015-034154 A | 2/2015 | | |
| JP | 2015-505713 A | 2/2015 | | |
| JP | 2015-058391 A | 3/2015 | | |
| KR | 10-2004-0090955 A | 10/2004 | | |
| KR | 10-2007-0104412 A | 10/2007 | | |

(Continued)

OTHER PUBLICATIONS

Norskov et al, Nature Chemistry, Towards the Computational Design of Solid Catalysts, 2009, 1, pp. 37-46. (Year: 2009).*

Rajan et al., Catalysis Science & Technology, "Vapour phase dehydration of glycerol over VPO catalyst supported on zirconium phosphate," vol. 4, No. 1, 2014, pp. 81-92.

Lauriol-Garbey et al., Journal of Catalysis., "New efficient and long-life catlyst for gas-phase glycerol dehydration to acrolein," vol. 281, No. 2, 2011, pp. 362-370.

* cited by examiner (Continued)

*Primary Examiner* — Paul A Zucker
(74) *Attorney, Agent, or Firm* — Dentons US LLP

(57) ABSTRACT

The present invention relates to a method for preparing acrylic acid from glycerin. More specifically, the present invention provides a method which can improve the selectivity of acrolein by applying a specific catalyst composition and process conditions to minimize the generation of coke carbon of the catalyst, and can prepare acrylic acid with higher productivity for a longer duration of time because a dehydration reaction can be performed for a longer working period while maintaining catalyst activity at a high level during the reaction.

7 Claims, 3 Drawing Sheets

(56) References Cited

FOREIGN PATENT DOCUMENTS

| KR | 10-2007-0104413 A | 10/2007 |
|----|-------------------|---------|
| KR | 10-1004593 B1 | 12/2010 |
| KR | 10-2011-0094198 A | 8/2011 |
| KR | 20120093853 A | 8/2012 |
| KR | 10-2012-0105029 A | 9/2012 |
| KR | 10-1248262 B1 | 3/2013 |
| KR | 10-2014-0015349 A | 2/2014 |
| KR | 10-2015-0006349 A | 1/2015 |
| KR | 20150009452 A | 1/2015 |
| KR | 10-2015-0037479 A | 4/2015 |
| KR | 101541934 B1 | 8/2015 |
| KR | 10-2016-0075321 A | 6/2016 |
| WO | 2004-007071 A1 | 1/2004 |
| WO | 2013084258 A1 | 6/2013 |
| WO | 2013084500 A2 | 6/2013 |

[FIG. 1]
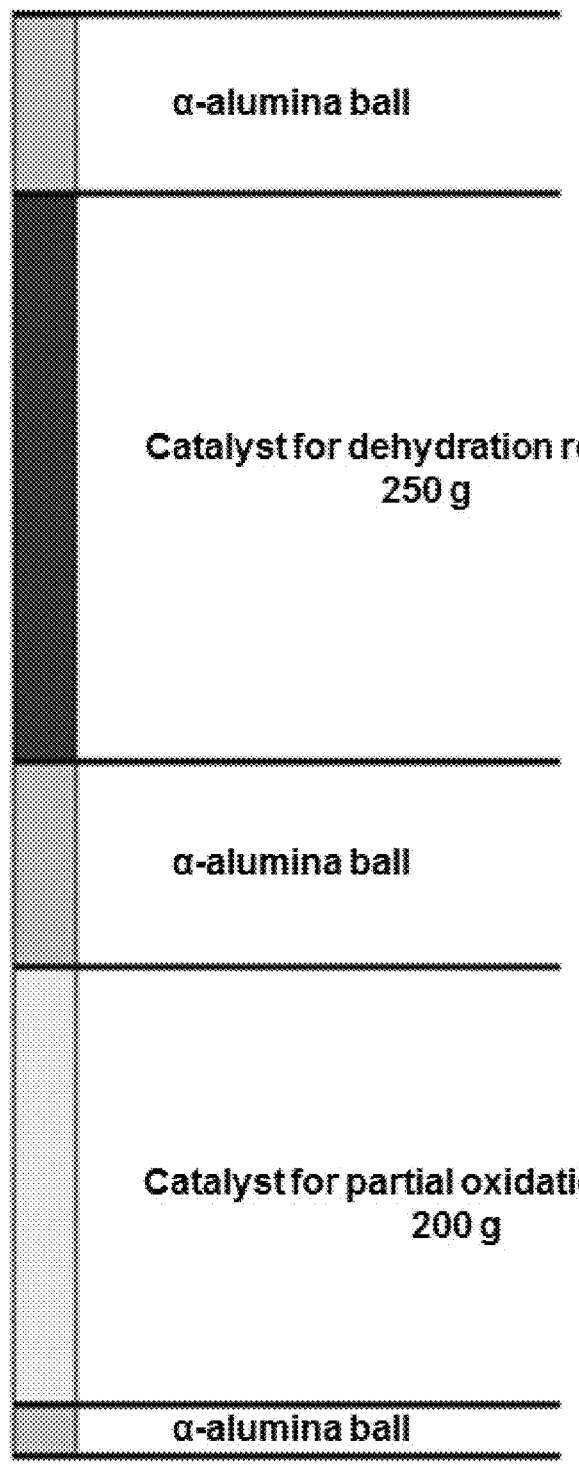

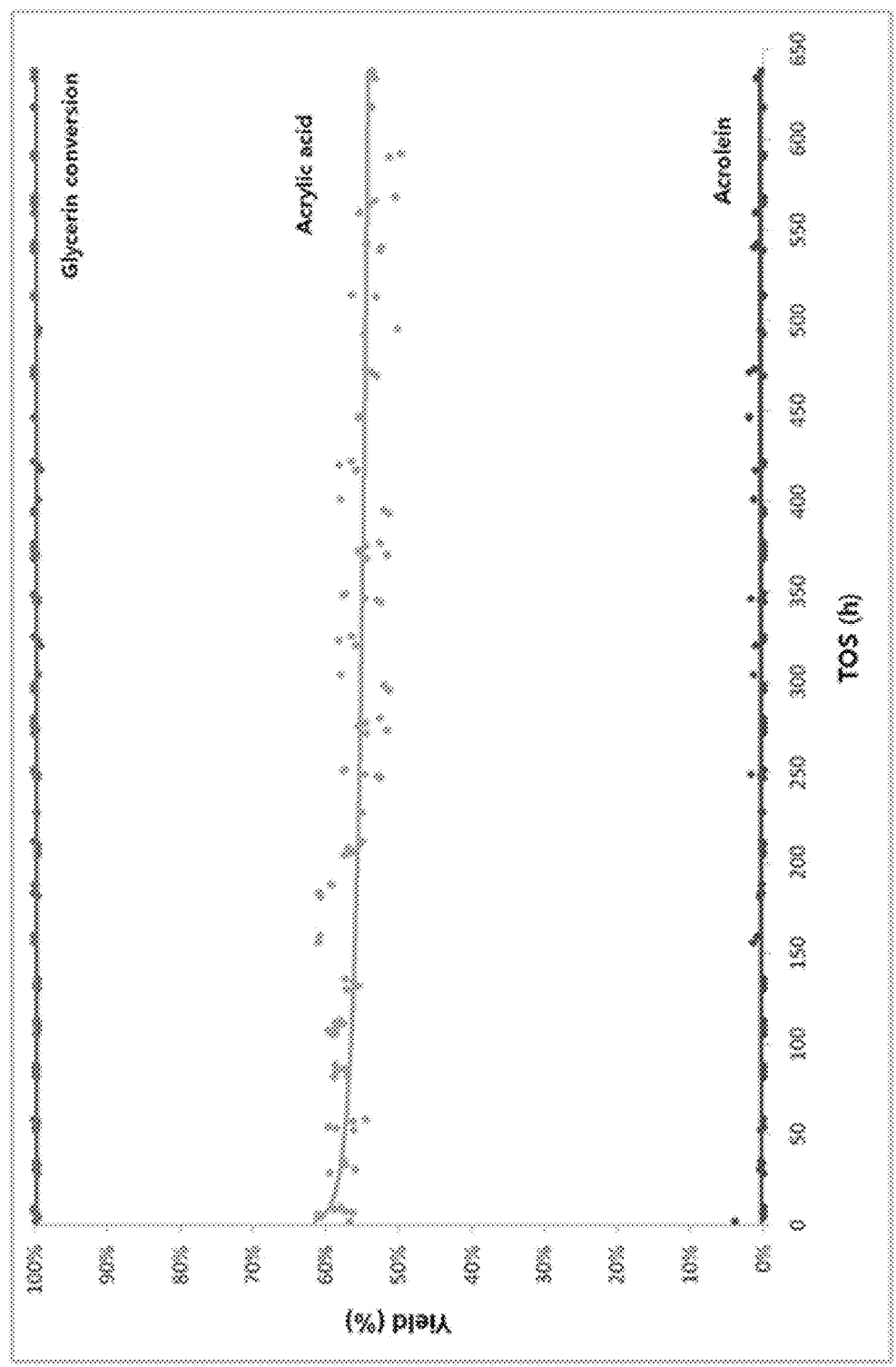
[FIG. 2]

[FIG. 3]
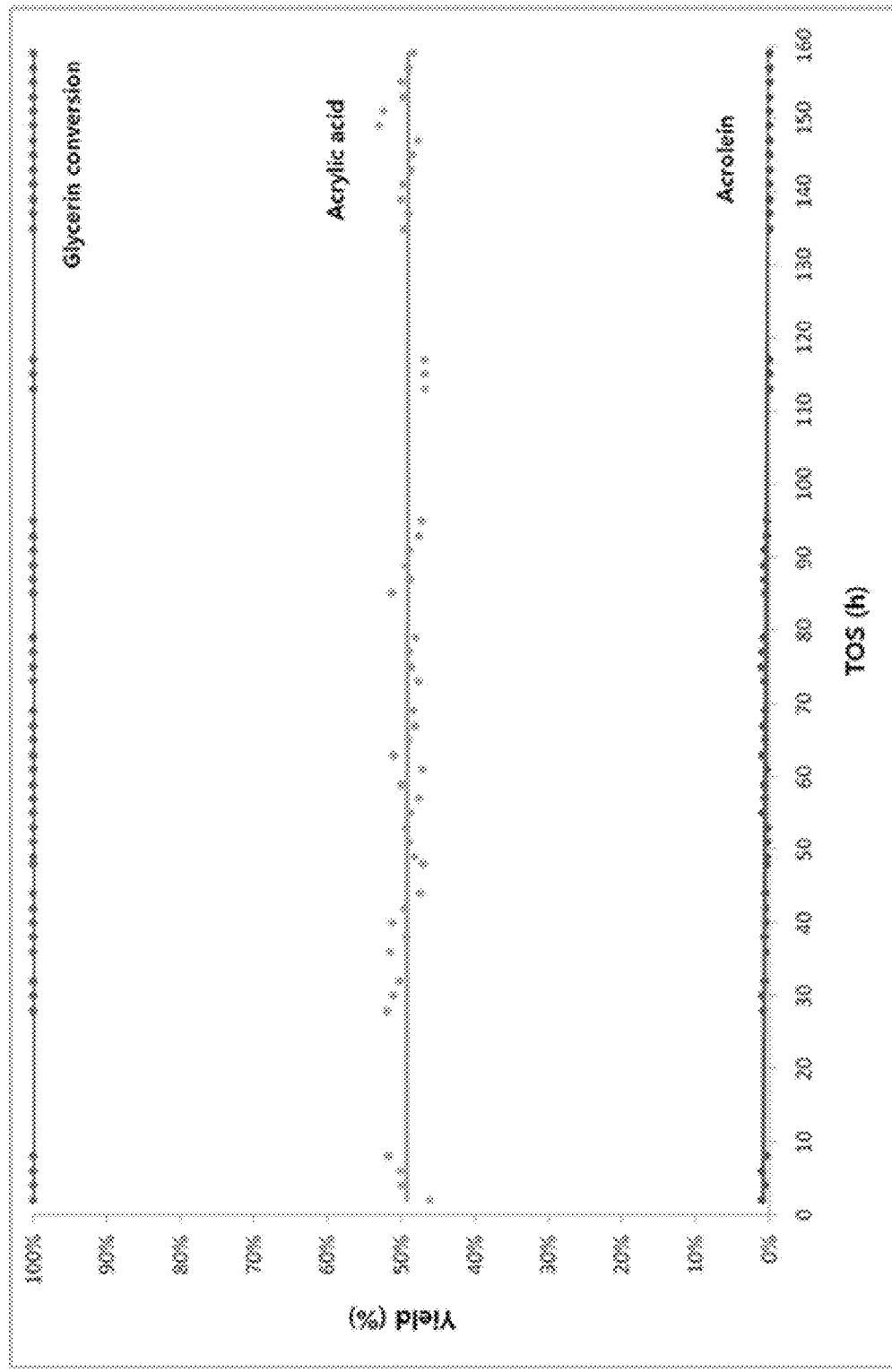

METHOD FOR PREPARING ACRYLIC ACID FROM GLYCERIN

CROSS-REFERENCE TO RELATED APPLICATIONS

This application is a 35 U.S.C § 371 national stage entry of international Application No. PCT/KR2016/014740, filed on Dec. 15, 2016, which claims priority to and the benefit of Korean Patent Application No. 10-2015-0184612 filed on Dec. 23, 2015 and Korean Patent Application No. 10-2016-0139259 filed on Oct. 25, 2016 with the Korean Intellectual Property Office, the disclosures of which are incorporated herein by reference in their entirety.

TECHNICAL FIELD

The present invention relates to a method for effectively preparing acrylic acid with high yield by using glycerin as a starting material while maintaining activity of a catalyst for a longer period of time.

BACKGROUND OF THE INVENTION

Catalytic reaction processes for producing acrylic acid using glycerin as a starting material consist of a glycerin dehydration reaction as the first step, and a partial oxidation reaction of acrolein as the second step. Since the two reactions occur in the presence of a catalyst, the use of a catalyst is essential.

However, the activity of a catalyst, in particular, the activity of a catalyst for the glycerin dehydration reaction, gradually decreases as the reaction proceeds, and one of major causes of such a decrease in catalytic activity is the loss of catalytic active sites due to the deposition of coke-like carbon produced during the reaction. Reduction in the activity of the catalyst leads to a decrease in the yield of acrylic acid as the final product, and thus, in order to commercially produce acrylic acid using glycerin, it is necessary to maintain the catalytic activity as long as possible. However, the existing patents related to the reaction for producing acrylic acid using glycerin mainly focus on the catalytic activity and merely include results of experiments performed for a relatively short period of time under mild reaction conditions, and thus the content related to the life span of the catalyst has not been properly addressed.

Meanwhile, it is possible to maintain the life span of a catalyst for a long period of time by adding a specific component to the catalyst and changing the reaction conditions and thereby oxidizing coke-like carbon produced in the catalyst for the glycerin dehydration reaction during the reaction in real time. However, acrolein, which is the product, and acrylic acid, can also be oxidized and removed under the reaction condition by which the coke carbon is oxidized, and thus it is necessary to establish a composition of the catalyst capable of selectively removing coke carbon without significantly affecting the product and the reaction conditions suitable for the composition.

DETAILS OF THE INVENTION

Objects of the Invention

It is one object of the present invention to provide a method for effectively preparing acrylic acid by maximizing the composition and reaction conditions of the catalyst such that the catalyst activity is maintained for a long period of time in the acrylic acid formation reaction using glycerin as a starting material.

Means for Achieving the Object

According to one embodiment of the present invention, a method for preparing acrylic acid is provided, including the steps of: subjecting glycerin to a dehydration reaction in the presence of a catalyst represented by Chemical Formula 1 below and oxygen or air; and carrying out a partial oxidation reaction of acrolein from the product obtained from the dehydration reaction, wherein in the dehydration reaction, the content of oxygen in a gaseous feed is 3.5 to 12 mol %, and the molar ratio of oxygen to glycerin (oxygen/glycerin) is 1 to 1.75.

$$Zr_a(M^1)_b(M^2)_cW_dP_eH_xO_y \quad \text{[Chemical Formula 1]}$$

In Chemical Formula 1, $M^1$ and $M^2$ may be the same or different, and each independently represent V, Fe, Nb, Zn, or a combination thereof, a, b, c, d, and e represent a composition ratio of the respective atoms, wherein a is 0.1 to 6, b/a is 0 to 1, c/a is 0 to 1, d/a is 0 to 1, and e/a is 0 to 10, among which at least one of b and c is not 0, and x and y are values of 0 to 10 which are determined according to the bonding state of crystallization water.

In one example, a may be 0.5 to 1, b may be 0.01 to 0.3, c may be 0.01 to 0.3, d may be 0.01 to 0.3, and e may be 1 to 5.

Specifically, the catalyst represented by Chemical Formula 1 may be $ZrZn_{0.02}W_{0.1}P_2H_xO_y$, $Zr_{0.9}Fe_{0.1}W_{0.1}P_2H_xO_y$, $Zr_{0.9}V_{0.1}W_{0.1}P_2H_xO_y$, $Zr_{0.9}Nb_{0.02}Fe_{0.1}W_{0.1}P_2H_xO_y$, $Zr_{0.9}Zn_{0.02}Fe_{0.1}W_{0.1}P_2H_xO_y$, $Zr_{0.9}Zn_{0.02}V_{0.1}W_{0.1}P_2H_xO_y$, $Zr_{0.9}Zn_{0.02}V_{0.1}W_{0.1}P_2H_xO_y$, $Zr_{0.8}Zn_{0.02}(FeV)_{0.1}W_{0.1}P_2H_xO_y$, $Zr_{0.8}Zn_{0.02}Fe_{0.2}W_{0.1}P_2H_xO_y$, $Zr_{0.8}Zn_{0.02}V_{0.2}W_{0.1}P_2H_xO_y$, or $Zr_{0.95}Zn_{0.02}V_{0.05}W_{0.1}P_2H_xO_y$, wherein x may be 2 to 6, and y may be 1 to 3.

The dehydration reaction may be carried out at a gas hourly space velocity (GHSV) of 100 to 5000 $h^{-1}$ and at a temperature of 250 to 350° C.

Further, in the dehydration reaction, the glycerin in the gaseous feed may be contained in an amount of 1 to 10 mol %.

In the present invention, the partial oxidation reaction of acrolein may be carried out in the presence of a catalyst represented by Chemical Formula 2 below and oxygen or air.

$$Mo_lW_mV_n(M^3)_q(M^4)_rO_z \quad \text{[Chemical Formula 2]}$$

In Chemical Formula 2, $M^3$ is Fe, Cu, Bi, Cr, Sn, Sb, or K, $M^4$ is an alkaline earth metal, l, m, n, q, r, and z represent an atomic ratio of Mo, W, V, A, B, and O, respectively, wherein l is 5 to 15, m/l is 0.15 to 0.4, n/l is 0.1 to 0.5, g/l is 0.1 to 0.4, r/l is 0 to 0.2, and z is a value determined according to the oxidation state of another element.

Further, the catalyst for the partial oxidation reaction of acrolein may be selected from the group consisting of $Mo_{12}W_2V_4Cu_2Sr_{0.5}O_z$, $Mo_{12}W_2V_4Fe_2Sr_{0.5}O_z$, $Mo_{12}W_2V_4Sb_2Sr_{0.5}O_z$, $Mo_{10}W_2V_3Cu_1Sr_{0.5}O_z$, $Mo_{10}W_2V_3Fe_1Sr_{0.5}O_z$, and $Mo_{10}W_2V_4Sb_1Sr_{0.5}O_z$.

In the method for preparing acrylic acid of the present invention, the yield of acrylic acid may be 50% or more and the yield of unreacted acrolein may be 0.5% or less when measured at the time when 640 hours or more have elapsed after the initiation of the reaction.

Effects of the Invention

According to the present invention, acrylic acid can be effectively prepared with a high yield for a long period of time by applying specific glycerin dehydration reaction catalyst and process conditions, thereby minimizing the generation of coke carbon of the catalyst and maintaining the catalytic activity at a high level during the reaction.

BRIEF DESCRIPTION OF DRAWINGS

FIG. 1 is a schematic diagram of a catalyst layer in a reactor of a reacting device for producing acrylic acid according to Example 2 of the present invention.

FIG. 2 is a graph showing the reaction results of acrylic acid production at an elapsed reaction time of 640 hours according to Example 1 of the present invention.

FIG. 3 is a graph showing the reaction results of acrylic acid production at an elapsed reaction time of 160 hours according to Example 2 of the present invention.

DETAILED DESCRIPTION OF THE EMBODIMENTS

In the present invention, it will be understood that the terms "first," "second," etc. may be used herein to describe various elements, and these terms are only used to distinguish one element from another element.

Further, the terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprise," "include," "have," etc. as used herein specify the presence of stated features, integers, steps, components, and/or combinations, but do not preclude the presence or addition of one or more other features, integers, steps, components, or combinations thereof.

The invention can be variously modified and take various forms, and thus specific embodiments are illustrated and described in detail below. It should be understood, however, that the invention is not intended to be limited to any particular disclosure form, but includes all modifications, equivalents, and alternatives falling within the spirit and scope of the invention.

Hereinafter, the method for preparing acrylic acid according to a preferred embodiment of the present invention will be described in detail.

According to one embodiment of the present invention, a method for preparing acrylic acid is provided, including the steps of: subjecting glycerin to a dehydration reaction in the presence of a catalyst represented by Chemical Formula 1 below and oxygen or air; and carrying out a partial oxidation reaction of acrolein from the product obtained from the dehydration reaction, wherein in the dehydration reaction, a content of oxygen in a gaseous feed is 3.5 to 12 mol %, and a molar ratio of oxygen to glycerin (oxygen/glycerin) is 1 to 1.75.

$$Zr_a(M^1)_b(M^2)_cW_dP_eH_xO_y \quad \text{[Chemical Formula 1]}$$

In Chemical Formula 1, $M^1$ and $M^2$ may be the same or different, and each independently represent V, Fe, Nb, Zn, or a combination thereof, a, b, c, d, and e represent a composition ratio of the respective atoms, wherein a is 0.1 to 6, b/a is 0 to 1, c/a is 0 to 1, d/a is 0 to 1, and e/a is 0 to 10, among which at least one of b and c is not 0, and x and y are values of 0 to 10 which are determined according to the bonding state of crystallization water.

In one example, a may be 0.5 to 1, b may be 0.01 to 0.3, c may be 0.01 to 0.3, d may be 0.01 to 0.3, and e may be 1 to 5.

Specifically, the catalyst represented by Chemical Formula 1 may be at least one selected from the group consisting of $ZrZn_{0.02}W_{0.1}P_2H_xO_y$, $Zr_{0.9}Fe_{0.1}W_{0.1}P_2H_xO_y$, $Zr_{0.9}V_{0.1}W_{0.1}P_2H_xO_y$, $Zr_{0.9}Nb_{0.02}Fe_{0.1}W_{0.1}P_2H_xO_y$, $Zr_{0.9}Zn_{0.02}Fe_{0.1}W_{0.1}P_2H_xO_y$, $Zr_{0.9}Zn_{0.02}V_{0.1}W_{0.1}P_2H_xO_y$, $Zr_{0.9}Zn_{0.02}V_{0.1}W_{0.1}P_2H_xO_y$, $Zr_{0.8}Zn_{0.02}(FeV)_{0.1}W_{0.1}P_2H_xO_y$, $Zr_{0.8}Zn_{0.02}Fe_{0.2}W_{0.1}P_2H_xO_y$, $Zr_{0.8}Zn_{0.02}V_{0.2}W_{0.1}P_2H_xO_y$, or $Zr_{0.95}Zn_{0.02}V_{0.05}W_{0.1}P_2H_xO_y$, wherein x may be 2 to 6, and y may be 1 to 3.

As described above, the dehydration reaction of glycerin according to a conventional method caused a problem in that the carbon-like carbon was deposited on the catalyst as the reaction proceeds, which then inactivated the catalyst, thereby shortening the lifespan of the catalyst. In particular, among the known acid catalysts, acid catalysts having many Brønsted acid centers have excellent production efficiency of acrolein, but a problem arises in that carbon is deposited on the acid catalyst during the dehydration reaction, and the catalyst is easily inactivated, and thus it is difficult to carry out the dehydration reaction for a long period of time.

One of the major causes of such a decrease in catalytic activity is the loss of catalytic active sites due to the deposition of coke carbon produced during the reaction. In particular, factors that influence the generation of coke carbon in the dehydration reaction of glycerin include reaction conditions such as reaction temperature, space velocity, oxygen and partial pressure of steam in the reactant, mass transfer in the catalyst by the catalyst pore structure, the number and intensity of an acid site on the catalyst surface, etc. The acid site of the catalyst is generally an active site that promotes a dehydration reaction. However, when strong acid sites are excessively present on the catalyst surface, coke carbon precursors are excessively produced by condensation between molecules due to side reactions, thereby causing a decrease in catalytic activity.

Accordingly, in order to solve the problems encountered in the prior arts, the present invention provides a method for effectively preparing acrylic acid with a high yield by applying a specific catalyst composition and process conditions, thereby inhibiting the production of coke carbon of the catalyst and effectively prolonging the life span of the catalyst.

The mixed oxide catalyst represented by Chemical Formula 1 may further include a metal represented by $M^1$ and $M^2$ in addition to zirconium, tungsten, and phosphorus. The $M^1$ and $M^2$ may play a role in inhibiting the production of coke carbon and byproducts, and may also convert the produced coke carbon into a COx material through an oxidation reaction with oxygen or steam and release them into the air. Through these processes, the deposition of coke carbon composed of phenol or polyaromatic compounds, which cause the deactivation of the catalyst, can be prevented, and thus the activity of the catalyst can be prolonged.

In particular, the present invention has a feature in that oxygen in the air fed together with glycerin to the feed, or pure oxygen and the transition metal atoms contained in the catalyst for glycerin dehydration, trigger an oxidation reaction to vaporize coke-type carbon impurities produced during the glycerin dehydration reaction, thereby preventing the coke from being deposited on the catalyst. Further, the present invention is characterized in preventing a reduction in yield of the products due to excessive oxidation reaction in the reaction for producing acrylic acid using glycerin.

For example, the catalyst represented by Chemical Formula 1 used in the dehydration reaction of glycerin may be at least one selected from the group consisting of $ZrZn_{0.02}W_{0.1}P_2H_xO_y$, $Zr_{0.9}Fe_{0.1}W_{0.1}P_2H_xO_y$, $Zr_{0.9}V_{0.1}W_{0.1}P_2H_xO_y$, $Zr_{0.9}Nb_{0.02}Fe_{0.1}W_{0.1}P_2H_xO_y$, $Zr_{0.9}Zn_{0.02}Fe_{0.1}W_{0.1}P_2H_xO_y$, $Zr_{0.9}Zn_{0.02}V_{0.1}W_{0.1}P_2H_xO_y$, $Zr_{0.9}Zn_{0.02}V_{0.1}W_{0.1}P_2H_xO_y$, $Zr_{0.8}Zn_{0.02}(FeV)_{0.1}W_{0.1}P_2H_xO_y$, $Zr_{0.8}Zn_{0.02}Fe_{0.2}W_{0.1}P_2H_xO_y$, $Zr_{0.8}Zn_{0.02}V_{0.2}W_{0.1}P_2H_xO_y$, and $Zr_{0.95}Zn_{0.02}V_{0.05}W_{0.1}P_2H_xO_y$.

The amount of the catalyst represented by Chemical Formula 1 may be appropriately adjusted depending on the amount and concentration of glycerin as the reactant. For example, the catalyst may be filled at a weight space velocity of 10 to 300 glycerin mmol/h·$g_{cat}$, preferably 10 to 100 glycerin mmol/h·$g_{cat}$, and more preferably 5 to 50 glycerin mmol/h·$g_{cat}$. When the amount of the catalyst is too small, the yield of the final acrylic acid may decrease due to the decrease in the conversion rate of glycerin. When the amount of the catalyst is too large, the production of impurities may be promoted due to an excessive increase in contact time, thereby reducing the yield of acrylic acid.

Meanwhile, in the glycerin dehydration reaction of the present invention, oxygen or air may be introduced together with the catalyst of Chemical Formula 1 into the glycerin feed as the reactant. First, when a glycerin aqueous solution is used as a glycerin source in the dehydration reaction, the concentration of the glycerin aqueous solution may be 80 wt % or less, or 25 to 80 wt %, and preferably 75 wt % or less. Herein, the amount of water vapor in the feed also plays an important role in inhibiting the formation of coke carbon, thus the concentration of the glycerin aqueous solution can be maintained at 80 wt % or less, and preferably 75 wt % or less. In addition, glycerin may be contained in the gaseous feed in an amount of 1 to 10 mol %, preferably 2 to 9 mol %, and more preferably 4 to 8 mol %. This indicates the concentration of glycerin in the gaseous feed containing oxygen and nitrogen in the glycerin aqueous solution, and the concentration of glycerin in the gaseous feed is maintained at the above-mentioned molar ratio with oxygen.

In particular, the gaseous feed may contain oxygen in an amount of 3.5 to 12 mol %, preferably 4.5 to 11 mol %, and more preferably 5 to 10 mol %. When the amount of oxygen in the gaseous feed is too high, the oxidation reaction of the products is accelerated, thereby causing a decrease in the yield of the entire process, and also safety issues may arise due to an excessive temperature rise in the reactor. In addition, when the amount of oxygen in the feed is too low, a problem arises in that the removal efficiency of the coke carbon produced on the catalyst during the reaction is reduced, and that the catalytic activity is easily deteriorated. Accordingly, controlling the concentration of oxygen contained in the feed within an appropriate range is very important for improving the yield of the entire process through the inhibition of a decrease in the catalytic activity.

Further, the molar ratio of oxygen to glycerin (oxygen/glycerin) present in the feed may be 1 to 1.75, preferably 1.1 to 1.65, and more preferably 1.15 to 1:5. When the amount of oxygen is too small compared to glycerin, the oxidation reaction does not sufficiently occur during the reaction, and the removal of coke carbon and the production of acrylic acid can be inhibited. When the amount of oxygen is excessively large compared to glycerin, the oxidation reaction may excessively occur. Accordingly, controlling the molar ratio of oxygen to glycerin contained in the feed within an appropriate range is very important for improving the yield of the entire process through the inhibition of a decrease in the catalytic activity.

In the present invention, the glycerin reaction process may be carried out at a gas hourly space velocity (GHSV) of 100 to 5000 $h^{-1}$, preferably 250 to 3000 $h^{-1}$, and more preferably 500 to 1000 $h^{-1}$.

In particular, in the glycerin reaction process, an increase in the gas hourly space velocity (GHSV) means that the amount of feed that can be treated per unit time and per catalyst increases, and therefore, when the reaction is carried out at a high GHSV, it means that the activity of the catalyst is excellent.

Furthermore, the step of reacting glycerin may be performed at 250 to 350° C., more preferably 280 to 320° C. The step of dehydrating glycerin is an endothermic reaction, and the reaction is preferably carried out within the temperature range in order to increase the yield of the final acrylic acid by producing acrolein with a high conversion rate and high selectivity. When the reaction temperature is too low, the conversion rate of glycerin may be reduced, and when the reaction temperature is too high, the selectivity of acrolein may be reduced due to excessive side reactions.

Meanwhile, in the present invention, after carrying out the dehydration reaction, a partial oxidation reaction of acrolein is carried out from the product obtained from the dehydration reaction to finally convert acrolein produced through the dehydration reaction of glycerin to acrylic acid.

Any catalyst commonly used in an acrolein partial oxidation can be used as the catalyst for the partial oxidation of acrolein. However, in view of securing high catalytic activity during the preparation of acrylic acid, a catalyst represented by Chemical Formula 2 below may be used.

$$Mo_lW_mV_n(M^3)_q(M^4)_rO_z \qquad \text{[Chemical Formula 2]}$$

In Chemical Formula 2, $M^3$ is Fe, Cu, Bi, Cr, Sn, Sb, or K, $M^4$ is an alkaline earth metal, l, m, n, q, r, and z represent an atomic ratio of Mo, W, V, A, B, and O, respectively, wherein l is 5 to 15, m/l is 0.15 to 0.4, n/l is 0.1 to 0.5, q/l is 0.1 to 0.4, r/l is 0 to 0.2, and z is a value determined according to the oxidation state of another element.

In one preferred example of Chemical Formula 2, as the catalyst for the partial oxidation reaction of acrolein, $M^3$ may be Cu, $M^4$ may be Sr, l may be 8 to 14, m/l may be 0.15 to 0.2, n/l may be 0.25 to 0.4, q/l may be 0.15 to 0.2, and r/l may be 0.01 to 0.06.

In one example, the catalyst of Chemical Formula 2 used in the partial oxidation reaction of acrolein may be at least one selected from the group consisting of $Mo_{12}W_2V_4Cu_2Sr_{0.5}O_z$, $Mo_{12}W_2V_4Fe_2Sr_{0.5}O_z$, $Mo_{12}W_2V_4Sb_2Sr_{0.5}O_z$, $Mo_{10}W_2V_3Cu_1$ 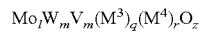 $Sr_{0.5}O_z$, $Mo_{10}W_2V_3Fe_1Sr_{0.5}O_z$, $Mo_{10}W_2V_4Sb_1Sr_{0.5}O_z$, etc.

Meanwhile, the partial oxidation reaction of acrolein may be performed in the presence of oxygen or air together with the catalyst of Chemical Formula 2. The partial oxidation reaction may be carried out at a gas hourly space velocity (GHSV) of 100 to 5000 $h^{-1}$, preferably 250 to 3000 $h^{-1}$, and more preferably 500 to 1000 $h^{-1}$. In addition, the partial oxidation reaction may be carried out at a temperature of 250 to 350° C., and more preferably 280 to 320° C. At this time, the gaseous feed may contain 5 to 10 mol % of oxygen.

The method for preparing acrylic acid according to the present invention can maintain a glycerin conversion rate of 100% and an acrylic acid yield of 50% or more when measured at the time when 640 hours or more have elapsed after the initiation of the reaction, and the reduction of acrylic acid yield relative to the initial stage of the reaction may be less than 5%. Further, in the case of unreacted acrolein, it may have a yield of 0.5% or less even at the time when 640 hours or more have elapsed after the initiation of the reaction.

Hereinafter, the preferred embodiments of the present invention will be described in more detail. However, these examples are given for illustrative purposes only, and the scope of the invention is not intended to be limited by these examples.

EXAMPLES

Example 1

1 g of an acrolein partial oxidation catalyst was filled into a stainless steel reactor having an inner diameter of 1 cm, then glass wool was filled therein, and 2 g of a dehydration catalyst was filled therein. Thereafter, the reactor was heated to the reaction temperature and fed with a gaseous feed. The detailed reaction conditions are shown in Table 1 below.

Example 2

As shown in FIG. 1, an a-alumina ball was filled into the lowermost part of a stainless steel reactor having an outer diameter of 1 inch and a height of 3 m, and 200 g of an acrolein partial oxidation catalyst supported on a silica-alumina ball was mixed with the a-alumina ball and filled therein. The a-alumina ball was again filled into the upper part of the partial oxidation catalyst layer, and then 250 g of a glycerin dehydration catalyst was mixed with the a-alumina ball and filled therein. Finally, the a-alumina ball was filled into the uppermost part of the reactor. Then, the reactor was heated up to the reaction temperature and then a gaseous feed was fed thereto. The detailed reaction conditions are shown in Table 1 below.

TABLE 1

| | Example 1 | Example 2 |
| --- | --- | --- |
| Reactor | Stainless steel having an inner diameter of 1 cm | Stainless steel having an outer diameter of 1 inch and a height of 3 m |
| Glycerin dehydration catalyst | $Zr_{0.9}Zn_{0.02}V_{0.1}W_{0.1}P_2H_xO_y$, 1 g | $Zr_{0.9}Zn_{0.02}V_{0.1}W_{0.1}P_2H_xO_y$, 250 g |
| Acrolein partial oxidation catalyst | $Mo_{12}W_2V_4Cu_2Sr_{0.5}O_z$, 2 g | $Mo_{12}W_2V_4Cu_2Sr_{0.5}O_z$, 200 g (silica-alumina ball supported catalyst) |
| Concentration of glycerin aqueous solution | 75 wt % | 75 wt % |
| Gas hourly space velocity: GHSV | 1500 $h^{-1}$ (Based on glycerin dehydration catalyst) | 1695 $h^{-1}$ (Based on glycerin dehydration catalyst) |
| Reaction temperature | 290° C. | 295° C. |
| Composition of gaseous feed | Glycerin 5.2%, oxygen 6.5%, vapor 8.9%, nitrogen 79.4% (molar ratio of oxygen/glycerin 1.25) | Glycerin 4.7%, oxygen 7%, vapor 8%, nitrogen 81% (molar ratio of oxygen/glycerin 1.49) |

Comparative Example 1

The preparation process of acrylic acid was carried out in the same manner as in Example 1, except that a heteropoly acid catalyst ($H_{0.5}Cs_{2.5}PW_{12}O_{40}$) was used.

Comparative Example 2

The preparation process of acrylic acid was carried out in the same manner as in Example 1, except that a heteropoly acid catalyst ($H_{1.5}Cu_{0.75}PW_{12}O_{40}$) was used.

Comparative Example 3

The preparation process of acrylic acid was carried out in the same manner as in Example 1, except that a heteropoly acid catalyst ($Cu_{1.5}PW_{12}O_{40}$) was used.

Comparative Example 4

The preparation process of acrylic acid was carried out in the same manner as in Example 1, except that the molar ratio of oxygen to glycerin (oxygen/glycerin) in the gaseous feed was changed to 0.8.

Comparative Example 5

The preparation process of acrylic acid was carried out in the same manner as in Example 1, except that the concentration of oxygen in the gaseous feed was changed to 2.7%.

Experimental Example: Evaluation of Performance of Preparation Process of Acrylic Acid The preparation process of acrylic acid was carried out according to Examples 1 and 2, and the reaction products were analyzed at the time at which 50 hours had elapsed after the reaction in the following manner, and the results of the analysis are shown in Table 2 below.

After the reaction, the products were condensed and collected, and the liquid product was analyzed by FID using GC, and non-condensable gas was analyzed by TCD. Then, the yield of acrylic acid and the yield of acrolein were measured according to the following Calculation Formulae 1 and 2.

Yield of acrylic acid(%)=(number of moles of acrylic acid produced/number of moles of glycerin fed)×100   [Calculation Formula 1]

Yield of acrolein(%)=(number of moles of acrolein produced/number of moles of glycerin fed)×100   [Calculation Formula 2]

TABLE 2

| | | Yield of acrylic acid (%) | Yield of acrolein (%) |
| --- | --- | --- | --- |
| Products obtained at the time | Example 1 | 58 | 0.1 |
| | Example 2 | 50 | 0.3 |
| | Comparative | 0 | 0.2 |

TABLE 2-continued

|  |  | Yield of acrylic acid (%) | Yield of acrolein (%) |
|---|---|---|---|
| when 50 hours had elapsed after the initiation of reaction | Example 1 | | |
| | Comparative Example 2 | 0 | 3 |
| | Comparative Example 3 | 0 | 3.2 |
| | Comparative Example 4 | 4.4 | 28.7 |
| | Comparative Example 5 | 27 | 8 |

As shown in Table 2 above, when the reaction products obtained in Example 1 and Example 2 according to the present invention were analyzed at the elapsed time of 50 hours, it can be confirmed that the yields of acrylic acid were excellent, showing the yields of 58% and 50%, respectively.

Further, FIG. 2 illustrates a graph showing the analysis results of the reaction products in the preparation process of acrylic acid carried out up to the time when a reaction time of 640 hours had elapsed according to Example 1 of the present invention. FIG. 3 illustrates a graph showing the analysis results of the reaction products in the preparation process of acrylic acid carried out up to the time when a reaction time of 160 hours had elapsed according to Example 2 of the present invention. As shown in FIGS. 2 and 3, Example 1 and Example 2 according to the present invention maintained a glycerin conversion rate of 100% and an acrylic acid yield of 50% or more even after an extended time of 640 hours or 160 hours had passed, and the reduction of acrylic acid yield relative to the initial stage of the reaction was less than 5%. In addition, it was confirmed that the unreacted acrolein showed a yield of 0.5% or less even at the termination of the reaction, confirming that the activity of the catalyst was maintained for a long time.

The invention claimed is:

1. A method for preparing acrylic acid comprising the steps of:
    subjecting glycerin to a dehydration reaction in the presence of a catalyst of Chemical Formula 1 below and oxygen or air, wherein the glycerin and oxygen or air are present in a gaseous feed; and
    carrying out a partial oxidation reaction of acrolein from a product obtained from the dehydration reaction in the presence of a catalyst of Chemical Formula 2 below and oxygen or air,
    wherein in the dehydration reaction, the content of oxygen in the gaseous reactant is 3.5 to 12 mol %, and the molar ratio of oxygen to glycerin (oxygen/glycerin) is 1 to 1.75:

$$Zr_a(M^1)_b(M^2)_cW_dP_eH_xO_y \quad \text{[Chemical Formula 1]}$$

wherein in Chemical Formula 1,
$M^1$ and $M^2$ are the same or different, and each independently represent is V, Fe, Nb, Zn, or a combination thereof,
each of a, b, c, d, and e is a composition ratio of the respective atoms, wherein a is 0.5 to 1, b is 0.01 to 0.3, c is 0.01 to 0.3, d is 0.01 to 0.3, and e is 1 to 5, and b/a is 0.01 to 0.6, c/a is 0.01 to 0.6, d/a is 0.01 to 0.6, and e/a is 1 to 10, and
x and y are values of 0 to 10 and depend on the amount of water of crystallization present in the catalyst of Chemical Formula 1;

$$Mo_lW_mV_m(M^3)_q(M^4)_rO_z \quad \text{[Chemical Formula 2]}$$

wherein in Chemical Formula 2,
$M^3$ is Fe, Cu, Bi, Cr, Sn, Sb, or K,
$M^4$ is an alkaline earth metal,
each of l, m, n, q, r, and z is an atomic ratio of Mo, W, V, $M^3$ and $M^4$ and O, respectively, wherein l is 5 to 15, m/l is 0.15 to 0.4, n/l is 0.1 to 0.5, q/l is 0.1 to 0.4, r/l is 0 to 0.2, and the value of z is determined according to the oxidation state of Mo, W, V, $M^3$ and $M^4$.

2. The method for preparing acrylic acid according to claim 1, wherein the catalyst of Chemical Formula 1 is at least one selected from the group consisting of $ZrZn_{0.02}W_{0.1}P_2H_xO_y$, $Zr_{0.9}Fe_{0.1}W_{0.1}P_2H_xO_y$, $Zr_{0.9}V_{0.1}W_{0.1}P_2H_xO_y$, $Zr_{0.9}Nb_{0.02}Fe_{0.1}W_{0.1}P_2H_xO_y$, $Zr_{0.9}Zn_{0.02}Fe_{0.1}W_{0.1}P_2H_xO_y$, $Zr_{0.9}Zn_{0.02}V_{0.1}W_{0.1}P_2H_xO_y$, $Zr_{0.8}Zn_{0.02}(FeV)_{0.1}W_{0.1}P_2H_xO_y$, $Zr_{0.8}Zn_{0.02}Fe_{0.2}W_{0.1}P_2H_xO_y$, $Zr_{0.8}Zn_{0.02}V_{0.2}W_{0.1}P_2H_xO_y$, and $Zr_{0.95}Zn_{0.02}V_{0.05}W_{0.1}P_2H_xO_y$, x is 2 to 6, and y is 1 to 3.

3. The method for preparing acrylic acid according to claim 1, wherein the dehydration reaction is carried out at a gas hourly space velocity (GHSV) of 100 to 5000 $h^{-1}$.

4. The method for preparing acrylic acid according to claim 1, wherein the dehydration reaction is carried out at a temperature of 250 to 350° C.

5. The method for preparing acrylic acid according to claim 1, wherein in the dehydration reaction, the amount of glycerin in the gaseous feed is 1 to 10 mol %.

6. The method for preparing acrylic acid according claim 1, wherein the catalyst of Chemical Formula 2 is at least one selected from the group consisting of $Mo_{12}W_2V_4Cu_2Sr_{0.5}O_z$, $Mo_{12}W_2V_4Fe_2Sr_{0.5}O_z$, $Mo_{12}W_2V_4Sb_2Sr_{0.5}O_z$, $Mo_{10}W_2V_3Cu_1Sr_{0.5}O_z$, $Mo_{10}W_2V_3Fe_1Sr_{0.5}O_z$, and $Mo_{10}W_2V_4Sb_1Sr_{0.5}O_z$.

7. The method for preparing acrylic acid according to claim 1, wherein the yield of acrylic acid is 50% or more, and the yield of unreacted acrolein is 0.5% or less when measured at the time when 640 hours or more have elapsed after the initiation of the reaction.

* * * * *